(12) United States Patent
Renevey et al.

(10) Patent No.: US 9,592,013 B2
(45) Date of Patent: Mar. 14, 2017

(54) METHOD FOR DETERMINING AN INSTANT VELOCITY OF A USER AND FOR IMPROVING ESTIMATION OF HEART RATE

(71) Applicant: CSEM Centre Suisse d'Electronique et de Microtechnique SA—Recherche et Developpement, Neuchatel (CH)

(72) Inventors: Philippe Renevey, Lausanne (CH); Olivier Grossenbacher, Neuchatel (CH)

(73) Assignee: CSEM CENTRE SUISSE D'ELECTRONIQUE ET DE MICROTECHNIQUE SA—RECHERCHE ET DÉVELOPPEMENT, Neuchâtel (CH)

( * ) Notice: Subject to any disclaimer, the term of this patent is extended or adjusted under 35 U.S.C. 154(b) by 20 days.

(21) Appl. No.: 14/627,327

(22) Filed: Feb. 20, 2015

(65) Prior Publication Data

US 2015/0238146 A1 Aug. 27, 2015

(30) Foreign Application Priority Data

Feb. 21, 2014 (EP) ..................................... 14156093

(51) Int. Cl.
*A61B 5/00* (2006.01)
*A61B 5/024* (2006.01)
(Continued)

(52) U.S. Cl.
CPC .......... *A61B 5/721* (2013.01); *A61B 5/02416* (2013.01); *A61B 5/02438* (2013.01);
(Continued)

(58) Field of Classification Search
CPC . A61B 5/721; A61B 5/02416; A61B 5/02438; A61B 5/1118; A61B 5/1123; A61B 5/681
See application file for complete search history.

(56) References Cited

U.S. PATENT DOCUMENTS

2009/0190713 A1 7/2009 Wai
2012/0006112 A1 1/2012 Lee et al.
(Continued)

FOREIGN PATENT DOCUMENTS

EP 1862765 A1 12/2007

OTHER PUBLICATIONS

Hutchinson, "Tracking Fitness With the "Heart Rate-Running Speed Index"", Runner's World, Feb. 1, 2014, XP002727770.
(Continued)

*Primary Examiner* — Scott Getzow
(74) *Attorney, Agent, or Firm* — Pearne & Gordon LLP

(57) ABSTRACT

The present disclosure concerns a method for determining an instant velocity of a user using a sensing device destined to be worn on an arm of the user and comprising a motion sensor for measuring a motion signal; the method comprising: measuring the motion signal and identifying when the user is performing a rhythmical activity; identifying when the user is walking or running; providing a relationship between the measured motion signal and corresponding motion features relating to a propulsive impulsion of a user's step; estimating a frequency of the user's step and a user-relative step length of the user using the motion features; and determining a user-relative instants velocity by combining the estimated step frequency and the estimated step length; the instant velocity being determined from the user-relative instant velocity using a calibration factor from the user-relative instant velocity using a calibration factor.

16 Claims, 2 Drawing Sheets

(51) Int. Cl.
  *G01C 22/00*   (2006.01)
  *A61B 5/11*    (2006.01)
  *G06K 9/00*    (2006.01)
  *A61B 5/0205*  (2006.01)

(52) U.S. Cl.
  CPC .......... *A61B 5/1118* (2013.01); *A61B 5/1123* (2013.01); *A61B 5/681* (2013.01); *G01C 22/006* (2013.01); *G06K 9/00342* (2013.01); *A61B 5/0205* (2013.01); *A61B 5/112* (2013.01); *A61B 5/4866* (2013.01); *A61B 5/6824* (2013.01); *A61B 5/7221* (2013.01); *A61B 2560/0223* (2013.01); *A61B 2562/0219* (2013.01)

(56) References Cited

U.S. PATENT DOCUMENTS

2012/0083705 A1   4/2012   Yuen et al.
2013/0080255 A1   3/2013   Li et al.

OTHER PUBLICATIONS

European Search Report for Application No. 14156093.8 dated Aug. 4, 2014.
Collins, Steven H., Peter G. Adamczyk, and Arthur D. Kuo. "Dynamic arm swinging in human walking", Proceedings of the Royal Society of London B: Biological Sciences (2009), Jul. 7, 2009.
Jackson, K. M., J. Joseph, and S.J. Wyard. "A Mathematical Model of Arm Swing During Human Locomotion", Journal of Biomechanics, Mar. 7, 1978, p. 277-289, vol. 11.6-7(1978), Pergamon Press Ltd. 1978, printed in Great Britain.

METHOD FOR DETERMINING AN INSTANT VELOCITY OF A USER AND FOR IMPROVING ESTIMATION OF HEART RATE

FIELD

The present invention concerns a method for determining an instant velocity of a user when walking or running using a sensing device destined to be worn on an arm of the user. The invention also related to using the instant velocity to improve a heart rate estimation measured with a heart rate sensor.

DESCRIPTION OF RELATED ART

Following the increasing market demand, different systems to estimate the speed of a runner (jogger, walker, etc.) have recently been developed. Such systems make use of different measurement principles, such as accelerometer measurement, the use of GPS, measuring Doppler radar or the principle of the pedometer.

Portable devices for estimating a speed of a runner usually comprise an accelerometer that is arranged such as to measure a vertical component of the acceleration. To that end, the accelerometer is placed on the shoe of the user or fastened to an ankle or knee of the user.

Other known methods for determining the speed of a runner use a measuring device that is located close to the runner's center of gravity. For example, an accelerometer can be fastened by means of a belt or clip close to the runner's center of gravity, such as the user's torso or head. Pedometers attachable to the pelvis or footwear and based on mechanical pendulums or accelerometers are also reported.

In EP1862765, an inertial sensor is placed in a wristwatch device at the wrists of a runner. However, the device is used solely for measuring the step frequency associated with the user's stepping. Indeed, the arms follow a very different trajectory from that of the user's center of mass and even briefly return backwards at each step. Such devices are possibly useful for approximately evaluating the distance traveled or the number of calories expended during a running session, but are however incapable of analyzing s step length accurately and, consequently the user's speed.

US2012083705 discloses an activity monitoring system comprising a fixture having size/shape adapted to couple to a location on the user's body and a particular signature; and a portable monitoring device adapted to detect the fixture's particular signature. The monitoring device includes a housing that is adapted to engage the fixture; activity sensors, disposed in the housing, to detect activity of the user and to generate data which is representative of the activity of the user; and processing circuitry, disposed in the housing, to calculate an activity-related quantity of the user using the data which is representative of the activity of the user, wherein the processing circuitry determines the monitoring device is engaging the fixture by detecting the fixture's particular signature, and, in response thereto, calculates the activity-related quantity using data from a set of the activity sensors.

US2012006112 discloses a method and apparatus of a portable terminal estimate a step length of a pedestrian. An accelerometer detects acceleration caused by a movement of the portable terminal as a pedestrian carrying the portable terminal walks. A gyroscope detects angular velocity caused by the movement of the portable terminal as the pedestrian walks. A controller determines a magnitude of a swinging motion of the portable terminal by using at least one of the detected acceleration and angular velocity, determines that the portable terminal makes the swinging motion when the magnitude of the swinging motion is equal to or greater than a predetermined value, determines a carrying position of the portable terminal in the pedestrian's body by using at least one of the detected acceleration and angular velocity, and estimates a step length of the pedestrian according to the determined carrying position of the portable terminal.

US2013080255 discloses step detection and step length estimation techniques include detecting salient points in sensor data of one or more sensors. A step frequency is estimated based on a time interval between the detected salient points. A step length of the step may then be computed based on a nonlinear combination of the estimated step frequency and a function of the sensor data, and/or a step model. Alternatively, the step length of the step may be computed based on a combination of a nonlinear function of the estimated step frequency and a (linear or nonlinear) function of the sensor data, and/or a step model.

The publication Tracking Fitness With the "Heart Rate-Running Speed Index" by Alex Hutchinson discloses an index which represents the different between the average speed of a run of a user to a theoretical speed calculated based on average heat rate of the user during the run. If the actual speed is faster than the predicted speed, it suggests an improvement in fitness since the baseline value of the index was calculated.

SUMMARY

One aim of the present invention is to propose a method free from the limitations of the known methods, in particular a method that makes it possible to determine in a simple manner a velocity of a runner (or walker) using a motion signal measured at the wrist of the user.

According to the invention, these aims are achieved notably by a method for determining an instant velocity of a user using a sensing device destined to be worn on an arm of the user and comprising a motion sensor for measuring and delivering a motion signal representative of the user's movements when the sensing device is worn; the method comprising:
  measuring the motion signal;
  identifying when the user is performing a rhythmical activity and estimating a fundamental movement frequency of the user from the measured motion signal;
  identifying when the user is walking or running by calculating an activity level of the user using the measured motion signal and the fundamental movement frequency;
  when the user is walking or running, providing a relationship between the measured motion signal and corresponding features of the user's motion which are indicative of a propulsive impulsion of a user's step, by using a bio-mechanical model of human locomotion;
  estimating a frequency of the user's step and estimating a user-relative step length of the user's step using the motion feature;
  determining a user-relative instant velocity by combining the estimated user's step frequency and the estimated user-relative step length; and
  determining the instant velocity from the user-relative instant velocity using a calibration factor.

In an embodiment, the instant velocity is used for estimating an a priori heart rate of the user, a distance traveled by the user, or an energy expenditure of the user.

In another embodiment, the proposed system is used in conjunction with an optical measurement system. An a priori estimation of the current heart rate in obtained by the combination of the estimated velocity and a model that relates heart rate and velocity. This a priori heart rate is then used to improve the robustness of the estimation of the heart rate using the optical signals when their quality is poor. Controversy, when the quality of the optical signals is good the model relating the velocity to the a priori heart rate is adapted to the specificities of the user.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS

Figure 1:
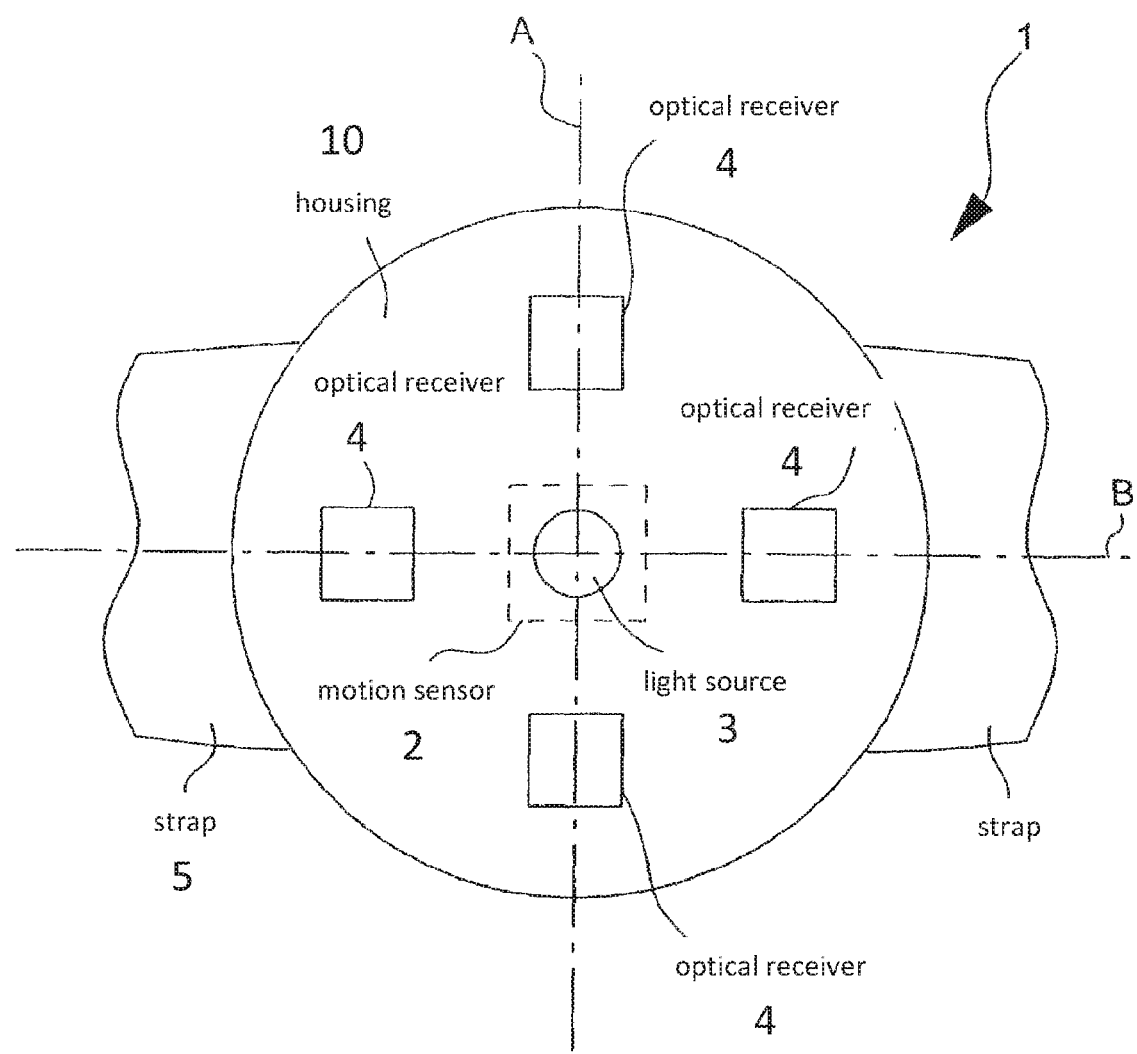
FIG. 1 illustrates schematically a sensor device for measuring a motion signal representative of the user's movements and a photoplethysmographic signal.

FIG. 1 illustrates schematically a sensor device 1 suitable for wearing on a wrist of user comprises a motion sensor 2 for measuring a motion signal representative of the user's movements. In the example of FIG. 1, the sensor device 1 is shown comprising a housing 10 and a strap 5 for attaching the sensor device 1 on the user's wrist. The motion sensor 2 is preferably adapted for measuring motion in three dimensions. For example, the motion sensor 2 can be a three dimensional accelerometer such as a MEMS-based accelerometer adapted to deliver an acceleration (or motion) signal along three axes. It will however be appreciated that other types of accelerometers or motion detecting devices can be used provided they deliver a reliable measure of motion. For example, the motion sensor 2 could be a gyro-sensor of any suitable technology incorporating a one or multi-dimensional accelerometer, or a rotating or vibrating. The motion sensor 2 can further comprise an ADC module (not shown) outputting acquired motion signal.

Although the sensor device 1 is shown as being worn on a wrist of the user, it is understood that the sensor device 1 is adapted to be worn on an arm of the user, for example at the wrist, somewhere around the arm or at any other location on the arm of the user. A different calibration factor for the sensor device 1 could however be needed depending on the possible different locations of the sensor device 1 on the arm.

Figure 2:
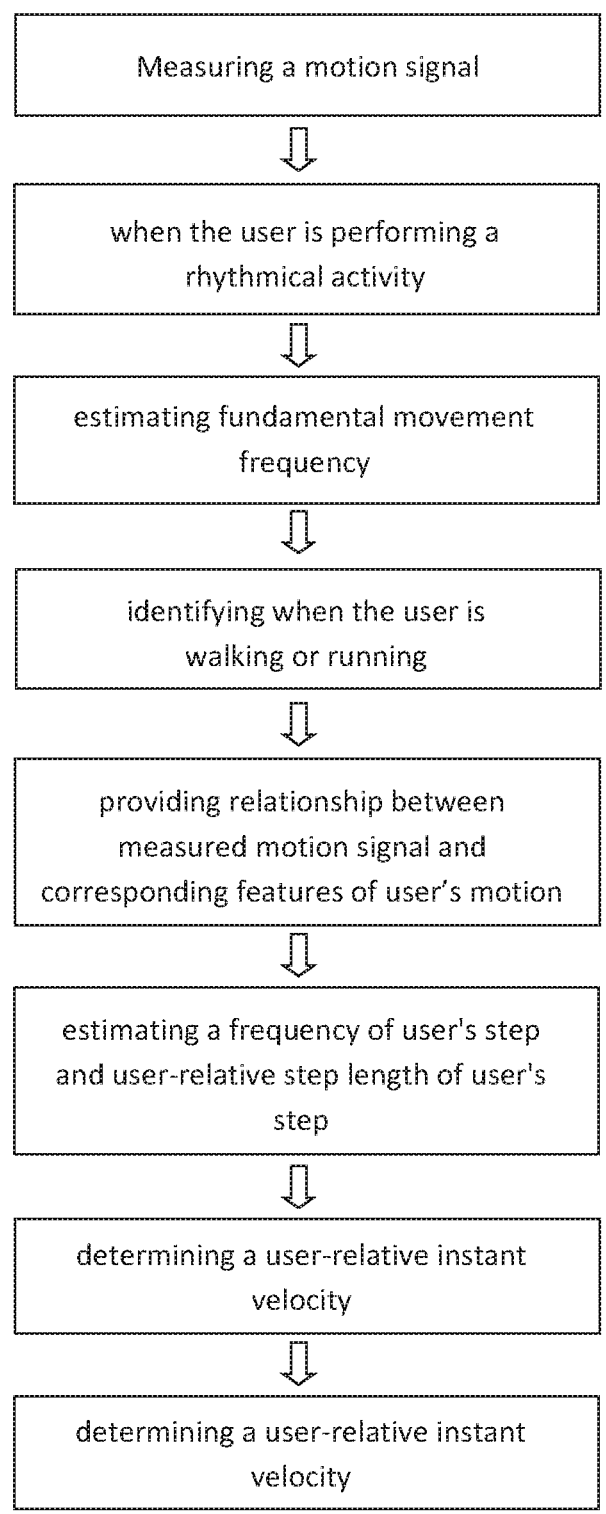
FIG. 2 illustrates a flow chart of a method for determining an instant velocity of the user.

In an embodiment illustrated in the flow chart of FIG. 2, a method for determining an instant velocity of the user using the sensing device 1 comprises:

providing the sensing device 1 on the arm of the user;
measuring the motion signal with the motion sensor 2;
identifying when the user is performing a rhythmical activity and estimating a fundamental movement frequency of the user from the measured motion signal;
identifying when the user is walking or running by calculating an activity level of the user using the measured motion signal and the 5 fundamental movement frequency;
when the user is walking or running, providing a relationship between the measured motion signal and corresponding motion features related to a propulsive impulsion of a user's step by using a bio-mechanical model of human locomotion; 10
estimating a frequency of the user's step and estimating user-relative step length of the user's step using the motion features;
determining a user-relative instant velocity by combining the estimated user's step frequency and the estimated user-relative step length; and
determining the instant velocity from the user-relative instant velocity using a calibration factor, e.g., by multiplying the user-relative instant velocity by the calibration factor.

Calculating an activity level of the user using the measured motion signal is carried out by calculating an energy value from the motion signal, for example using the norm of the motion signal. The calculated energy value can be compared with a threshold energy such that when the calculated energy value is equal or below the threshold energy the user can be considered at rest. Conversely, when the calculated energy value is above the threshold energy the user can be considered as performing an activity.

In the case the calculated energy value is above the threshold energy, calculating an activity level can further comprise detecting segments of the measured motion signal having rhythmical characteristics, for example, by frequency spectral analysis of the motion signal. The fundamental movement frequency can then be extracted from the motion signal through one of the following technique: zero-crossing, parametric or non-parametric spectral estimation, autocorrelation, recurrence plots, and adaptive filters.

The fundamental movement frequency can then be combined with the calculated energy in order to differentiate between an activity level of the user corresponding to walking, running or another type of rhythmical activity. For example, the ratio of the fundamental movement frequency over the calculated energy can be used for identifying when the user is walking or running. The classification of the activity when a rhythmical motion is detected is based on two features: the amplitude of the motion and the motion frequency. The orientation of the device in the gravity field can be used as an additional feature (generally the fore-arm is close to vertical during walking and close to horizontal during running). Classical classification methods such as Bayesian classifiers, artificial neural network (ANN) of hidden Markov models (HMM) can be used. If not explicitly included in the model (such as in HMM) constraints have to be applied to the output of the classification system in order to discard short duration events (such as checking the display of the device) that would result in misclassification errors and lead to erroneous estimation of the estimated velocity.

During walking or running, the position of the user's legs relatively to the floor can be divided into two phases: on-floor (impact of the user's foot on the ground) and off-floor (propulsive impulsion of the user's step or propulsive phase). This alternate of impact and propulsive phases produce a rotation moment on the trunk that has to be compensated in order to provide an efficient locomotion. This compensation is provided by a counter-moment provided by the arms moving in anti-phase with the legs. The estimation of the counter-moment produced by the arms is related to the moment produced by the impact and the propulsion phases of the legs. The compensation further depends on the mass and the length of the user's arms as well as on the angle of the elbow. The inertia moment is related to the mass distribution relatively to the center of rotation. The arm has two degrees of freedom: the shoulder and the elbow. The shoulder is the center of rotation for the damping system (arm). Depending on the velocity and on the walking/running preferences of the user the elbow's angle can vary between approximately 180° (generally during walking activity) and approximately 90° (generally during running activity). The changes of the elbow's angle modify the mass distribution relatively to the shoulder rotation center and therefore modify the inertia moment of the arm. In the present invention the orientation of the motion sensor 2 relatively to the gravity field is used to estimate the angle of the elbow and to compensate the value of the inertia moment of the arm accordingly.

In an embodiment, the bio-mechanical model comprises an active damper model wherein the arms act as an active damper of the torque produced by the propulsive phase of the legs. In other words, the model comprises a damper model provided by the motion of the arm, wherein the damper model is active to damp the torque produced by the propulsive phase of the legs of the user. The angle of the elbow can be used in the active damper model to compensate the inertia moment of the arm accordingly to the different position of the arm. For example, the arm positions are different between walking and running.

In another embodiment, the step frequency is estimated by using the motion features. The step frequency can be estimated either by the estimation of time intervals between repetitive events in the acceleration signal (e.g. maxima, minima or zero-crossings), by applying an adaptive filter to track the dominant frequency or by applying a spectral transformation such as Fourier transform and by determining the dominant frequency.

The step length is dependent on the user, i.e., user's leg length, user's weight, user's running style, etc. Therefore, a user-relative step length is first estimated by using the motion features. A step length can then be determined by using a user-specific calibration. For example, the user-relative step length can be multiplied by a user-specific calibration factor.

The user-specific calibration factor can be obtained by performing a calibration session where an average velocity is measured. The user-specific calibration factor is then calculated as the ratio of the measured average velocity over the user-relative instant. Alternatively, the calibration factor is obtained by performing a calibration session where a distance traveled by the user is measured. The calibration factor is then calculated as the ratio of the measured distance over a user-relative distance.

In another variant, the calibration factor is estimated by using morphological parameters of the user in combination with an empirically determined model. The model has to be determined by using measurements from a sufficiently large population of users that spans over the selected set of morphological parameters. The morphological parameters can comprise any one of: gender, age, weight, height, legs' length of the user, or a combination of two or more of the parameters.

The user-relative instant velocity can be determined by multiplying the estimated step frequency with the estimated step length. The instant velocity can then be obtained by multiplying the relative velocity by the calibration factor.

In an embodiment, the distance traveled by the user is estimated by using the instant velocity. The estimated distance can then be used for estimating the step length.

In another embodiment, an energy expenditure of the user is calculated using the instant velocity. For example, the user's energy expenditure can correspond to the instant velocity multiplied by the weight of the user.

In yet another embodiment, the method further comprises a step of estimating an a priori heart rate of the user using the determined instant velocity and a model relating the heart rate value with the instant velocity. The a priori heart rate can be determined using a linear or nonlinear relationship between the determined instant velocity and the heart rate value. The relationship between velocity and heart rate can be identified using recordings of a representative population of users for different running speeds. Since such regressions are user dependent, the method can further comprise the step of using a physiological model including one of age, gender, weight or height of the user.

In yet another embodiment, the sensing device 1 further comprises a heart rate sensor for measuring a heart rate signal when the sensing device 1 is worn on the arm of the user. The heart rate sensor can be any suitable device for measuring a heart rate signal such as a photoplethysmographic sensor, an electrocardiogram (ECG) or any heart rate estimation system. The a priori heart rate can then be used as additional information about heart rate to improve the measured heart rate estimated from the heart rate signal when the quality of the heart rate signal degrades. In the example of FIG. 1, the heart rate sensor is a photoplethysmographic (PPG) sensor 3, 4 adapted to measure a PPG signal when the sensing device 1 is worn on the user's arm. The motion sensor 2 and the heart rate sensor can be placed in the sensor device 1 such as to form an integrated sensor device. In this latter configuration, the motion signal is better correlated with the measured PPG signal than if the motion sensor 2 is placed further from the multichannel PPG sensor.

A reliability of the measured heart rate can be determined such as to determine when the measured heart rate reliable or unreliable (for example due to motion artifacts). In the case where the measured heart rate is unreliable, the a priori heart rate can be used in combination with the measured heart rate such as to obtain a more robust value for the measured heart rate.

The a priori heart rate supplies additional information for the estimation of the measured heart rate. For example, when the heart rate sensor fails to estimate the measured heart rate with sufficient reliability, the a priori heart rate can be used to improve the performance of the heart rate sensor. On the other hand, when the heart rate sensor estimates a measured heart rate with sufficient reliability, the measured heart rate obtained from the heart rate sensor can be used alone. Such a reliable measured heart rate obtained during walking or running can be used to adapt the model relating the velocity to the motion heart rate to the user's specificities.

In an embodiment, the a priori heart rate is used to filter the measured heart rate around the value of the a priori heart rate.

In an embodiment not represented, the sensor device 1 further comprises a display arranged for displaying the measured heart rate and/or a priori heart rate. The display can be arranged on the arm of the user, for example by being integrated to the sensor device 1 itself, or in any other location of the user. The display can be further arranged for displaying any other information including the calculated activity level, the determined instantaneous velocity, the energy expenditure, or the estimated traveled distance.

REFERENCE NUMBERS

1 sensor device
2 motion sensor 3 light source
4 optical receiver
5 strap
10 housing
A first axe
B second axe

The invention claimed is:

1. Method for determining an instant velocity of a user using a sensing device destined to be worn on an arm of the user and comprising a motion sensor for measuring and delivering a motion signal representative of the user's movements when the sensing device is worn; the method comprising:

measuring the motion signal;
identifying when the user is performing a rhythmical activity and estimating a fundamental movement frequency of the user from the measured motion signal;
identifying when the user is walking or running by calculating an activity level of the user using the measured motion signal and the fundamental movement frequency;
when the user is walking or running, providing a relationship between the measured motion signal and corresponding features of the user's motion which are indicative of a propulsive impulsion of a user's step, by using a bio-mechanical model of human locomotion comprising an active damper model wherein the user's arms act as an active damper of torque produced by a propulsive phase of the user's legs;
estimating a frequency of the user's step and estimating a user-relative step length of the user's step using the motion features;
determining a user-relative instant velocity by combining the estimated user's step frequency and the estimated user-relative step length; and
determining the instant velocity from the user-relative instant velocity using a calibration factor.

2. Method according to claim 1, wherein the calibration factor is determined using one of: cumulated distance when the user is walking or running, average velocity of the user when walking or running, or a morphological parameter of the user.

3. Method according to claim 1, wherein said estimating a step frequency comprises identifying a time of impact of the user's foot using the motion features.

4. Method according to claim 1, wherein said estimating a step length further comprises using a calibration measurement taken at the determined instantaneous velocity or at an estimated traveled distance by the user.

5. Method according to claim 1, wherein combining the estimated step frequency and the estimated step length comprised multiplying the estimated step frequency with the estimated step length.

6. Method according to claim 1, further comprising multiplying the estimated user-relative step length by a user-specific calibration factor.

7. Method according to claim 5, wherein the calibration factor is obtained by measuring an average velocity or a distance traveled by the user when the user is walking or running.

8. Method according to claim 5, wherein the calibration factor is estimated by using morphological parameters of the user in combination with an empirically determined model.

9. Method according to claim 1, further comprising estimating an a priori heart rate of the user by using the determined instant velocity and a model relating a heart rate value with the instant velocity.

10. Method according to claim 9, wherein the model comprises a linear or a nonlinear relationship between the determined instants velocity and said heart rate value.

11. Method according to claim 9, wherein the model comprises a physiological model including one of age, gender, weight or height of the user.

12. Method according to claim 9, wherein the sensing device further comprises a heart rate sensor adapted to measure a heart rate signal when the sensing device is worn; and wherein the method further comprises measuring the heart rate signal and estimating a measured heart rate from the measured heart rate signal.

13. Method according to claim 12, wherein said estimating a measured heart rate comprises determining a reliability of the measured heart rate; and wherein the a priori heart rate is used in combination with the measured heart rate when the measured heart rate is unreliable.

14. Method according to claim 13, further comprising user-specifically adapting the model by using the measured hear rate when the measured heart rate is reliable.

15. Method according to claim 1, further comprising estimating a distance traveled by the user by using the integration of the determined instant velocity.

16. Method according to claim 1, further comprising calculating an energy expenditure of the user by using the determined instant velocity.

* * * * *